United States Patent
Ju

(10) Patent No.: US 9,927,805 B2
(45) Date of Patent: Mar. 27, 2018

(54) METHOD AND APPARATUS FOR MANUFACTURING RADIATION INTENSITY BOLUS

(71) Applicant: SAMSUNG LIFE PUBLIC WELFARE FOUNDATION, Seoul (KR)

(72) Inventor: Sang Gyu Ju, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 894 days.

(21) Appl. No.: 14/376,306

(22) PCT Filed: Feb. 1, 2013

(86) PCT No.: PCT/KR2013/000848
§ 371 (c)(1),
(2) Date: Aug. 1, 2014

(87) PCT Pub. No.: WO2013/115607
PCT Pub. Date: Aug. 8, 2013

(65) Prior Publication Data
US 2015/0006098 A1  Jan. 1, 2015

(30) Foreign Application Priority Data
Feb. 2, 2012   (KR) ........................ 10-2012-0010812

(51) Int. Cl.
*G05B 19/418* (2006.01)
*A61N 5/10* (2006.01)
(Continued)

(52) U.S. Cl.
CPC ......... *G05B 19/41875* (2013.01); *A61N 5/10* (2013.01); *A61N 5/1075* (2013.01);
(Continued)

(58) Field of Classification Search
CPC .. G05B 19/41875; B33Y 80/00; Y02P 10/295
(Continued)

(56) References Cited

U.S. PATENT DOCUMENTS 8,121,253 B2 * 2/2012 Nelms .................... A61N 5/103
250/492.3
8,263,954 B2 * 9/2012 Iwata ....................... G21K 1/10
250/492.3
(Continued)

FOREIGN PATENT DOCUMENTS

EP       2116278 A1    11/2009
JP     2002-102366 A    4/2002
(Continued)

OTHER PUBLICATIONS

Cho et al., "The Benefit of Individualized Custom Bolus in the Postmastectomy Radiation Therapy: Numerical Analysis with 3-D Treatment Planning," *Department of Radiation Oncology* 21(1):82-93, 2003.
(Continued)

*Primary Examiner* — Ricky Ngon
(74) *Attorney, Agent, or Firm* — Seed IP Law Group LLP

(57) ABSTRACT

Disclosed are a method and an apparatus for manufacturing a radiation intensity bolus. The method comprises the steps of: (a) calculating, by a radiotherapy treatment planning unit, a received 3D radiation dose distribution, planning a bolus to be manufactured, and outputting radiation intensity modulation information; (b) receiving, by a bolus design unit, the radiation intensity modulation information, generating a conversion file for manufacturing bolus, and outputting information about a 3D structure of the bolus to be manufactured; (c) receiving, by a bolus manufacturing unit, the conversion file for manufacturing bolus, verifying a type, location, and size of the bolus to be manufactured, sending the verified data to a 3D printer, and manufacturing the
(Continued)

bolus; and (d) obtaining, by an accuracy verification unit, information about a 3D structure of the manufactured bolus and evaluating manufacturing accuracy by comparing the information about the 3D structure of the manufactured bolus with the information about the planned bolus.

22 Claims, 4 Drawing Sheets

(51) Int. Cl.
*B33Y 80/00* (2015.01)
*G21K 1/10* (2006.01)
*G21K 1/04* (2006.01)
*B22F 3/105* (2006.01)
*B29C 64/00* (2017.01)

(52) U.S. Cl.
CPC .............. *B33Y 80/00* (2014.12); *A61N 5/103* (2013.01); *A61N 2005/1087* (2013.01); *A61N 2005/1095* (2013.01); *A61N 2005/1096* (2013.01); *B22F 3/1055* (2013.01); *B29C 64/00* (2017.08); *G21K 1/046* (2013.01); *G21K 1/10* (2013.01); *Y02P 10/295* (2015.11)

(58) Field of Classification Search
USPC .......................................................... 702/84
See application file for complete search history.

(56) References Cited

U.S. PATENT DOCUMENTS

| 2008/0027974 A1 | 1/2008 | Collins |
| 2010/0195793 A1 | 8/2010 | Nelms |
| 2011/0309250 A1 | 12/2011 | Appleby et al. |

FOREIGN PATENT DOCUMENTS

| JP | 2004-291625 A | 10/2004 |
| JP | 2005-237694 A | 9/2005 |
| JP | 2009-148494 A | 7/2009 |
| KR | 20110039514 A | 4/2011 |
| WO | 2011/024085 A1 | 3/2011 |

OTHER PUBLICATIONS

Park et al., "Utilization of Tissue Compensator for Uniform Dose Distribution in Total Body Irradiation," *J. Korean Soc Ther Radiol* 12(2):233-241, 1994.

* cited by examiner

[Fig. 1]
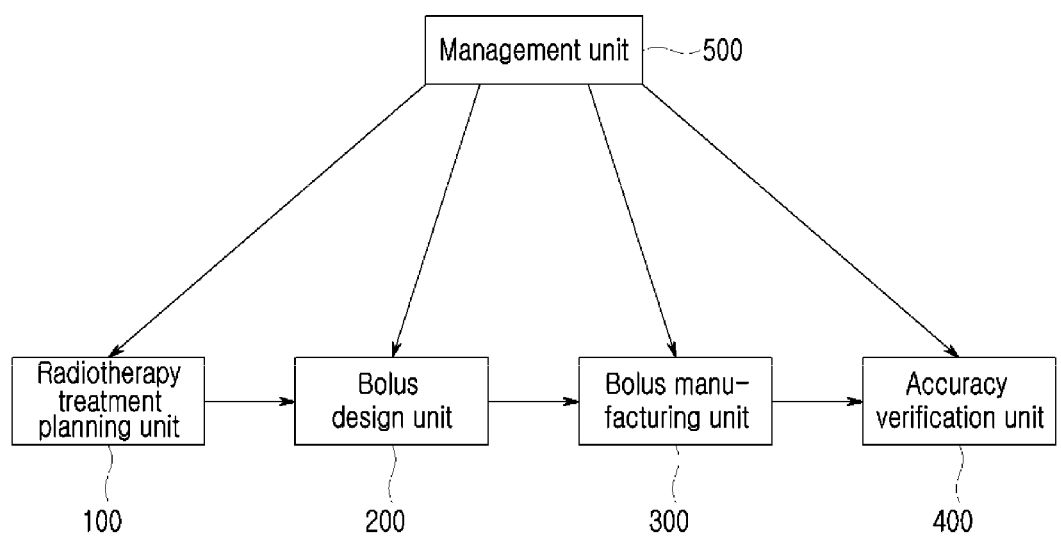

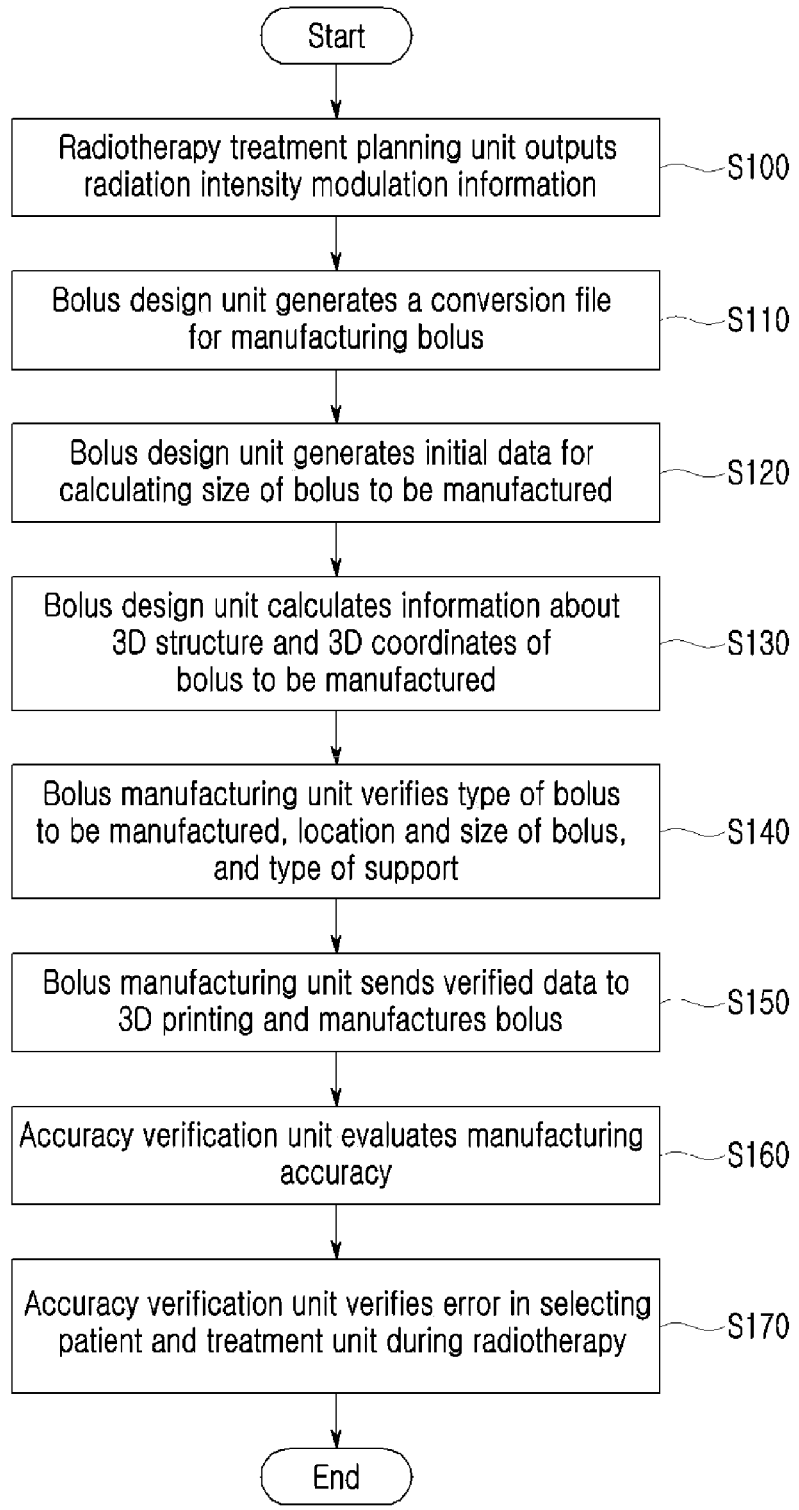

[Fig. 3]
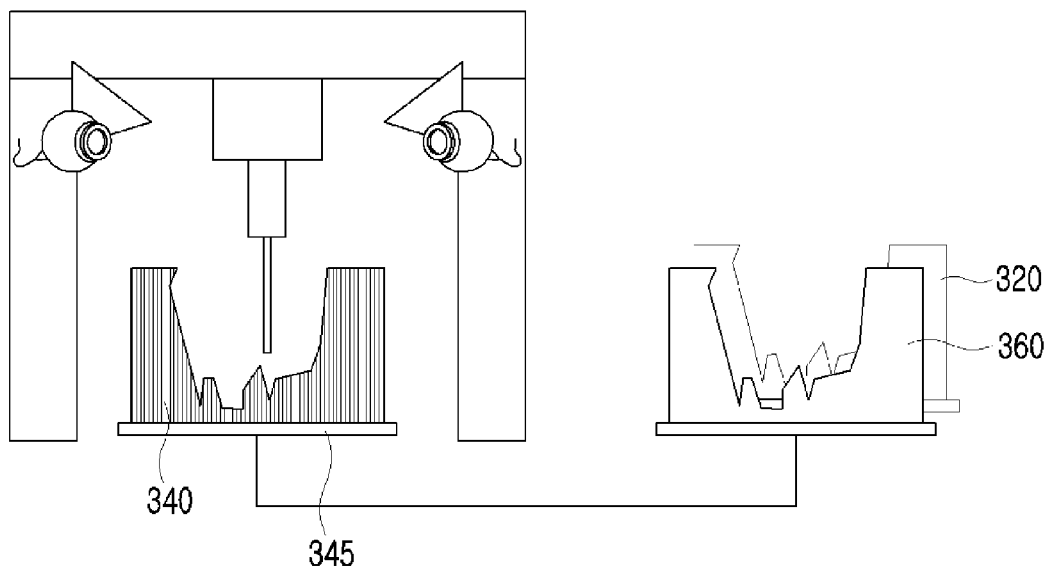
[Fig. 4]
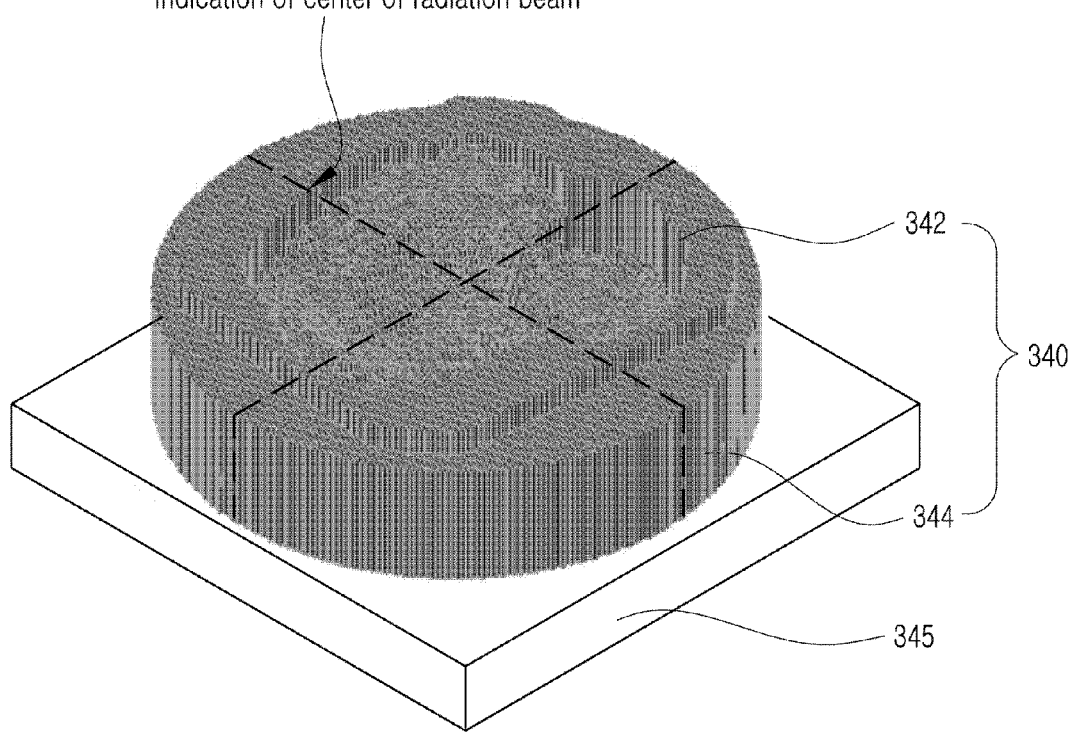

[Fig. 5]
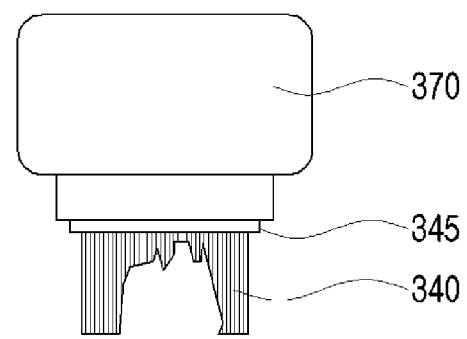
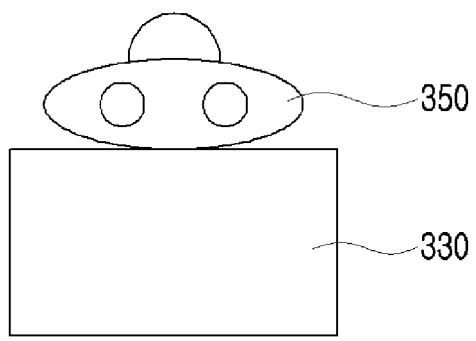

METHOD AND APPARATUS FOR MANUFACTURING RADIATION INTENSITY BOLUS

TECHNICAL FIELD

The present disclosure relates to a method and apparatus for manufacturing a radiation intensity bolus, and more particularly, to a method and apparatus for manufacturing a radiation intensity bolus, which are capable of manufacturing a radiation intensity bolus so that the bolus can be made in a desired shape using a 3D printer based on radiation dose modulation information obtained by calculating a radiation dose in radiotherapy.

BACKGROUND ART

In general, a radiation intensity bolus is a material that is placed in the center of a radiation beam, or placed in contact with or inserted into the body of a patient in order to modulate a radiation dose distribution of radiotherapy.

The radiation intensity bolus is used to increase a tumor radiation dose and to protect surrounding normal tissues by modulating the intensity of radiation in radiotherapy. It is used for electron beam, X-ray, proton, and particle beam radiotherapies. Particularly for the proton and particle beam radiotherapy, the radiation intensity bolus is necessary in order to obtain a radiation dose distribution suitable for the shape of a tumor.

Furthermore, the radiation intensity bolus is used to improve the quality of an image through enhanced beam quality when an image is obtained using radiation since it is effective in adjusting the radiation dose and irradiated region by controlling the intensity of a specific region or blocking the radiation.

Recently, proton and particle beam radiotherapy facilities have become very popular. Since the National Health Insurance has started to cover intensity modulated radiotherapy in Korea, a simple method for intensity modulated radiotherapy is required.

However, conventional intensity modulated radiotherapy uses a radiation collimator for shielding radiation entirely or partially to obtain desired intensity modulated radiation or a bolus made by cutting using milling.

When using a radiation collimator, an error may occur due to the malfunction of the collimator, and it is difficult to calculate a scattered dose occurring in collimator gaps or leaves. It increases the duration of treatment and also increases uncertainty during the radiotherapy of moving organs.

The latter is free from the above disadvantages, but it is difficult to be used in medical facilities due to severe noise from cutting process, generation of contaminated coolant, need for a wide space to accommodate cutting facilities, and the difficulty of high-precision processing.

DISCLOSURE

Technical Problem

An object of the present disclosure is to provide a method for manufacturing a radiation intensity bolus, wherein manufacture of a bolus is planned by calculating a 3D radiation dose distribution using a radiation dose computed by a radiotherapy treatment planning apparatus or manually, information about the 3D structure of the bolus to be manufactured is obtained using radiation intensity modulation information, the type, location, and size of the bolus to be manufactured are verified, the bolus is manufactured through a 3D printer, and manufacturing accuracy is evaluated by comparing information about the manufactured bolus with information about the planned bolus.

Another object of the present disclosure is to provide an apparatus for manufacturing a radiation intensity bolus, which uses the method for manufacturing a radiation intensity bolus according to the present disclosure.

Technical Solution

A method of manufacturing a radiation intensity bolus according to the present disclosure for achieving the object includes steps of (a) calculating, by a radiotherapy treatment planning unit, a received 3D radiation dose distribution, planning a bolus to be manufactured, and outputting radiation intensity modulation information; (b) receiving, by a bolus design unit, the radiation intensity modulation information, generating a conversion file for manufacturing bolus, and outputting information about a 3D structure of the bolus to be manufactured; (c) receiving, by a bolus manufacturing unit, the conversion file for manufacturing bolus, verifying a type, location, and size of the bolus to be manufactured, sending the verified data to a 3D printer, and manufacturing the bolus; and (d) obtaining, by an accuracy verification unit, information about a 3D structure of the manufactured bolus and evaluating manufacturing accuracy by comparing the information about the 3D structure of the manufactured bolus with the information about the planned bolus.

In the method of manufacturing a radiation intensity bolus according to the present disclosure, the step (b) may include steps of calculating, by the bolus design unit, information about a thickness of each pixel of the bolus to be manufactured that is proportional to an amount of radiation intensity modulation; generating, by the bolus design unit, initial data by which the size of the bolus to be manufactured is calculated; generating, by the bolus design unit, an initial bolus of the bolus to be manufactured based on the initial data; and calculating, by the bolus design unit, information about the 3D structure and information about 3D coordinates of the bolus to be manufactured based on the initial bolus.

In the method of manufacturing a radiation intensity bolus according to the present disclosure, the step (b) may include generating a periphery support that surrounds a periphery of the bolus to be manufactured and supports the bolus to be manufactured while the bolus is manufactured; and generating an attachment unit that attaches and fixes the manufactured bolus to a treatment unit.

In the method of manufacturing a radiation intensity bolus according to the present disclosure, it is preferable that the information about the 3D coordinates is 3D location coordinates where the bolus to be manufactured is placed based on an indication of a center of a radiation beam and an origin of the 3D location coordinates and axes of the 3D location coordinates are indicated on a surface of the bolus to be manufactured.

In the method of manufacturing a radiation intensity bolus according to the present disclosure, the step (c) may include reading, by the bolus manufacturing unit, the conversion file for manufacturing the bolus, verifying the type, location, and size of the bolus to be manufactured, and verifying a type of the attachment unit; and sending, by the bolus manufacturing unit, the verified data to the 3D printer and manufacturing the bolus comprising the periphery support.

In the method of manufacturing a radiation intensity bolus according to the present disclosure, the step (c) may comprise including the attachment unit in the computed structure of the bolus so that the attachment unit and the bolus are manufactured simultaneously.

In the method of manufacturing a radiation intensity bolus according to the present disclosure, the step (d) may include displaying, by the accuracy verification unit, the bolus stored in the conversion file for manufacturing bolus during radiotherapy treatment so that an error in selecting a patient or a treatment unit is verified.

In the method of manufacturing a radiation intensity bolus according to the present disclosure, the step (d) may include steps of obtaining a periphery structure of the manufactured bolus and reconfiguring the manufactured bolus in a format to be compared with the planned bolus; overlapping a 3D structure of the reconfigured bolus with a 3D structure of the planned bolus based on an indication of a center of a radiation beam and calculating a difference in a thickness in each pixel of the bolus; and evaluating the manufacturing accuracy by diagramming the difference in the thickness in numbers and graphics.

In the method of manufacturing a radiation intensity bolus according to the present disclosure, the periphery structure may be obtained using any one of a 3D laser scanner, a video camera, and a touch sensor.

In the method of manufacturing a radiation intensity bolus according to the present disclosure, the step (d) includes steps of mounting the manufactured bolus on a treatment unit, irradiating the manufactured bolus, and obtaining a radiation distribution that has passed through the manufactured bolus; measuring the obtained radiation distribution, overlapping the measured radiation distribution with the radiation intensity modulation information based on an indication of a center of a radiation beam, and performing a comparison between differences of radiation intensities of pixels of the bolus; and diagramming the difference in the intensity in numbers and graphics and evaluating the manufacturing accuracy.

In the method of manufacturing a radiation intensity bolus according to the present disclosure, the radiation distribution may be obtained using any one of a film, an electronic portal imaging apparatus, and a radiation distribution measurement apparatus.

In the method of manufacturing a radiation intensity bolus according to the present disclosure, in the size of the bolus to be manufactured is determined by calculating the 3D structure of the bolus to be manufactured in accordance with a distance inverse square law based on a location where the bolus to be manufactured is attached to a treatment unit, an radiation source, and a distance from a patient.

In the method of manufacturing a radiation intensity bolus according to the present disclosure, the 3D radiation dose distribution may be calculated using a radiotherapy treatment planning apparatus or manually.

In the method of manufacturing a radiation intensity bolus according to the present disclosure, the size of the bolus to be manufactured may be determined again after calculating an attenuation of radiation according to materials of the bolus to be manufactured using an attenuation coefficient or a stopping power ratio depending on the type of radiation.

In the method of manufacturing a radiation intensity bolus according to the present disclosure, the conversion file for manufacturing bolus may store at least one of the type of material used to calculate the size of the bolus to be manufactured, a 3D structure, location coordinates, information identifying a corresponding patient, information about a treatment unit, and a radiation port.

An apparatus for manufacturing a radiation intensity bolus according to the present disclosure for achieving another object includes: a radiotherapy treatment planning unit that calculates a received 3D radiation dose distribution, plans a bolus to be manufactured, and outputs radiation intensity modulation information; a bolus design unit that receives the radiation intensity modulation information, generates a conversion file for manufacturing bolus, and outputs information about a 3D structure of the bolus to be manufactured; a bolus manufacturing unit that receives the conversion file for manufacturing bolus, verifies a type, location, and size of the bolus to be manufactured, sends the verified data to a 3D printer, and manufactures the bolus; and an accuracy verification unit that obtains information about a 3D structure of the manufactured bolus and evaluates manufacturing accuracy by comparing the information about the 3D structure of the manufactured bolus with the information about the planned bolus.

The bolus design unit of the apparatus for manufacturing a radiation intensity bolus according to the present disclosure may calculate information about a thickness of each pixel of the bolus to be manufactured that is proportional to an amount of radiation intensity modulation, generate initial data by which the size of the bolus to be manufactured is calculated, generate an initial bolus of the bolus to be manufactured based on the initial data, and calculate information about the 3D structure and information about 3D coordinates of the bolus to be manufactured based on the initial bolus.

The bolus design unit of the apparatus for manufacturing a radiation intensity bolus according to the present disclosure may generate a periphery support that surrounds a periphery of the bolus to be manufactured and supports the bolus to be manufactured while the bolus is manufactured, and generate an attachment unit that attaches and fixes the manufactured bolus to a treatment unit.

The bolus manufacturing unit of the apparatus for manufacturing a radiation intensity bolus according to the present disclosure may read the conversion file for manufacturing the bolus, verify the type, location, and size of the bolus to be manufactured, and verify a type of the attachment unit; and send the verified data to the 3D printer and manufacture the bolus comprising the periphery support.

The bolus manufacturing unit of the apparatus for manufacturing a radiation intensity bolus according to the present disclosure may include the attachment unit in the computed structure of the bolus so that the attachment unit and the bolus are manufactured simultaneously.

The accuracy verification unit of the apparatus for manufacturing a radiation intensity bolus according to the present disclosure may display the bolus stored in the conversion file for manufacturing the bolus during radiotherapy treatment so that an error in selecting a patient or a treatment unit is verified.

The accuracy verification unit of the apparatus for manufacturing a radiation intensity bolus according to the present disclosure may obtain a periphery structure of the manufactured bolus and reconfigure the manufactured bolus in a format to be compared with the planned bolus, overlap a 3D structure of the reconfigured bolus with a 3D structure of the planned bolus based on an indication of a center of a radiation beam and calculate a difference in a thickness in each pixel of the bolus, and evaluate the manufacturing accuracy by diagramming the difference in the thickness in numbers and graphics.

The accuracy verification unit of the apparatus for manufacturing a radiation intensity bolus according to the present disclosure may mount the manufactured bolus on a treatment unit and irradiate the manufactured bolus so that the radiation passes through the manufactured bolus, measure a distribution of the transmitted radiation, overlap the measured radiation distribution with the radiation intensity modulation information based on an indication of a center of a radiation beam, and perform a comparison between differences of radiation intensities of pixels of the bolus, and diagram the difference in the intensity in numbers and graphics and evaluates the manufacturing accuracy.

Advantageous Effects

In accordance with the present disclosure, an error due to the malfunction of a radiation collimator when an intensity modulated radiotherapy is performed through control of the opening and shutting of the radiation collimator can be prevented, an error in the calculation of a scattered dose generated in collimator gaps or leaves can be prevented, the treatment time can be significantly reduced compared to a conventional method using a collimator, and an intensity modulated beam can be accurately radiated when a moving internal organ is treated.

Furthermore, compared to a bolus manufacturing method using conventional cutting, noise generated in a cutting process can be reduced, the generation of a contaminated coolant can be prevented, bolus manufacturing is performed in a small space, and precision processing is available which prevents micromachining errors due to the size of a cutting drill.

When a radiation intensity bolus is manufactured by 3D printing, metal effective in radiation shielding can be used as well as tissue-equivalent materials.

DESCRIPTION OF DRAWINGS

FIG. 1 is a block diagram of an apparatus for manufacturing a radiation intensity bolus for implementing a method for manufacturing a radiation intensity bolus according to the present disclosure.

FIG. 2 is a flowchart illustrating the method for manufacturing a radiation intensity bolus according to the present disclosure.

FIG. 3 illustrates a configuration according to an embodiment of an accuracy verification step in the method for manufacturing a radiation intensity bolus according to the present disclosure.

FIG. 4 is a perspective view of an actually manufactured bolus 340 and an attachment unit 345 illustrated in FIG. 3.

FIG. 5 illustrates a configuration according to another embodiment of the accuracy verification step in the method for manufacturing a radiation intensity bolus according to the present disclosure.

DETAILED DESCRIPTION

Hereinafter, embodiments of a method and apparatus for manufacturing a radiation intensity bolus according to the present disclosure are described with reference to the accompanying drawings.

FIG. 1 is a block diagram of an apparatus for manufacturing a radiation intensity bolus for implementing a method for manufacturing a radiation intensity bolus according to the present disclosure. The apparatus includes a radiotherapy treatment planning unit 100, a bolus design unit 200, a bolus manufacturing unit 300, an accuracy verification unit 400, and a management unit 500.

The function of each of the blocks of the apparatus for manufacturing a radiation intensity bolus for implementing a method for manufacturing a radiation intensity bolus according to the present disclosure is described below with reference to FIG. 1.

The radiotherapy treatment planning unit 100 computes a 3D radiation dose distribution calculated using a radiotherapy treatment planning apparatus or manually and outputs radiation intensity modulation information.

The bolus design unit 200 generates the structure of a 3D bolus using an attenuation coefficient and a stopping power ratio, and determines the size of the bolus using the beam source of a treatment unit, a location to which the bolus will be attached, and the location of a tumor within a patient.

The bolus manufacturing unit 300 reads information about the structure of a planned radiation intensity bolus, verifies the size of the bolus to be manufactured and the type of attachment unit to which a treatment unit will be attached using ID information, mounts corresponding materials, and prints the planned bolus.

The accuracy verification unit 400 obtains 3D structure information, such as information about the thickness and size of a manufactured bolus and coordinates in each thickness, evaluates manufacturing accuracy by comparing the obtained 3D structure information with information about the planned bolus, and verifies an error in the selection of a patient and an error in the selection of a treatment unit using a patient ID and information related to a treatment unit.

The management unit 500 manages a series of sequential processes of planning the radiotherapy treatment, designing the radiation intensity bolus, manufacturing the radiation intensity bolus, and verifying manufacturing accuracy, displays results, and sends data using a network.

FIG. 2 is a flowchart illustrating the method for manufacturing a radiation intensity bolus according to the present disclosure.

FIG. 3 illustrates the configuration of the accuracy verification unit 400 according to an embodiment of an accuracy verification step in the method for manufacturing a radiation intensity bolus according to the present disclosure. The accuracy verification unit 400 includes the bolus manufacturing unit 300, a planned bolus 320, an actually manufactured bolus 340, an attachment unit 345, and obtained 3D structure information 360.

FIG. 4 is a perspective view of the actually manufactured bolus 340 and the attachment unit 345 illustrated in FIG. 3. The actually manufactured bolus 340 includes information 342 about the thickness of each cell and a periphery support 344.

FIG. 5 illustrates a configuration according to another embodiment of the accuracy verification step in the method for manufacturing a radiation intensity bolus according to the present disclosure, and includes a patient treatment table 330, a patient 350, the actually manufactured bolus 340, the attachment unit 345, and a treatment unit 370.

The operation of the method for manufacturing a radiation intensity bolus using a 3D printer according to the present disclosure is described below with reference to FIGS. 1 to 5.

The radiotherapy treatment planning unit 100 computes a 3D radiation dose distribution, obtains radiation intensity modulation information, and plans a bolus (S100). In this case, the radiation includes X-rays, and electron, proton and particle beam, and the calculation of a radiation dose may be performed using a radiotherapy treatment planning apparatus or manually.

The bolus design unit 200 reads the computed radiation intensity modulation information from the radiotherapy treatment planning unit 100, and generates a conversion file for manufacturing the planned bolus 320 in a 3D printer (S110).

The bolus design unit 200 generates the attachment unit 345, computes the thickness information 342 of each pixel of the bolus to be manufactured that is proportional to the amount of radiation intensity modulation on the plane of the attachment unit 345, reconfigures the bolus to be manufactured in a 3D way, and generates initial data by which the size of the bolus may be calculated (S120).

Furthermore, the bolus design unit 200 generates the periphery support 344 in a circle or a square shape that may be attached to and supported by the periphery of the actually manufactured bolus 340. The periphery support 344 surrounds the periphery of the bolus while not entrenching the area of the actually manufactured bolus 340, and functions to support the actually manufactured bolus 340 when the bolus is generated.

In this case, in relation to the size of the bolus, the 3D structure of the bolus is computed and determined in accordance with a distance inverse square law based on a location where the bolus is attached to the treatment unit 370, a radiation source, and the distance from a patient. The thickness and size of the bolus may be recalculated depending on the materials of the bolus. The attenuation of radiation according to materials is recalculated using an attenuation coefficient or a stopping power ratio depending on the type of radiation used, and the thickness of the bolus is determined again.

That is, the degree of radiation attenuation per thickness of the bolus is previously measured, and the thickness of the bolus is calculated in proportion to the desired amount of intensity modulation. Accordingly, if an attenuation coefficient or stopping power ratio previously measured and input by a user is input in a library form and the materials of the bolus that may be easily used by a user is selected, the attenuation of radiation is suitably computed again and the bolus is generated.

In this case, the attachment unit 345 may be designed according to a predetermined user treatment unit 370, may be included in the computed structure of the bolus, and may be included in the design of the bolus so that the attachment unit 345 can be manufactured at the same time as that the bolus is manufactured. The attachment unit 345 refers to fixing means for attaching the manufactured bolus 340 to the treatment unit 370.

The bolus design unit 200 generates an initial bolus for calculating the size of the bolus to be manufactured based on the initial data, generates the 3D structure of the bolus based on the generated initial bolus, calculates the coordinates of a 3D location where the bolus is placed based on the indication of the center of a radiation beam as illustrated in FIG. 4, and diagrams the calculated coordinates on the actually manufactured bolus 340 (S130).

Furthermore, the bolus design unit 200 marks the location of the center of the bolus and its product on a surface of the actually manufactured bolus 340 based on the indication of the center of the radiation beam so that a user is easily aware of the insertion direction and insertion location of the actually manufactured bolus 340.

In this case, the conversion file includes information about the type of corresponding materials based on information about the attenuation coefficient and stopping power ratio of materials used for the calculation, information about the 3D structure of the computed bolus, location coordinates, information about a corresponding recognized patient, information about the treatment unit 370, and a radiation port. This is printed on a surface of the bolus when the bolus is manufactured in response to a user's selection.

The bolus manufacturing unit 300 reads received information about the manufactured bolus, verifies whether manufactured bolus is the bolus to be manufactured using corresponding patient ID information, reads information about the materials of the bolus, mounts the corresponding materials, and verifies information about the location and size of the bolus to be manufactured (S140).

The bolus manufacturing unit 300 verifies whether the type of attachment unit 345 is corrected using information about the treatment unit 370 to be used, sends the verified data to a 3D printing system, and manufactures the bolus including the attachment unit 345 attached to the manufactured bolus 340 using a printing technology using the mounted corresponding materials (S150).

In this case, at step S100, the center mark and mounting direction of the actually manufactured bolus 340 is printed on a surface of the actually manufactured bolus 340 based on the information about the planned bolus on the basis of the mark information and the indication of the center of the radiation beam including the information about the patient.

The accuracy verification unit 400 obtains 3D structure information, such as information about the thickness and size of the manufactured bolus 340 and coordinates in each thickness using a 3D laser scanner, a video camera, a touch sensor, or an X-ray detector as illustrated in FIG. 3, and evaluates manufacturing accuracy by comparing the obtained 3D structure information with the information about the bolus 320 that has been planned at step S100 (S160).

That is, a method of verifying manufacturing accuracy by the accuracy verification unit 400 may be divided into a method of verifying the contour of the periphery of the actually manufactured bolus 340 and a method of verifying penetration amounts measured after radiation is transmitted.

The method of verifying the contour of the periphery of the actually manufactured bolus 340 includes obtaining the periphery structure of the actually manufactured bolus 340 using a 3D laser scanner, a video camera, or a touch sensor, and reconfiguring the obtained periphery structure in the same format as that that may be compared with the planned bolus 320 in a 3D way.

Thereafter, the 3D structure of the planned bolus 320 is overlapped with the 3D structure of the actually manufactured bolus 340 based on the indication of the center of the radiation beam. A difference in the thickness in each pixel of the bolus is computed and diagrammed in the form of numbers and graphics so that a difference in the thickness in each location may be checked.

In the expression of the difference in the thickness, information about an error of the thickness in all the pixels of the bolus may be expressed using a typical statistical scheme including the mean or a standard deviation.

To help user's judgment, a reference value can be input through an input window on a screen and only a difference in the thickness that exceeds a reference value can be displayed. A function of calculating a gamma value based on an error of a thickness and distance input through the input window and graphically displaying a part that exceeds the calculated gamma value is also provided.

The method of verifying penetration amounts measured after irradiation includes mounting the actually manufactured bolus 340 on the treatment unit 370, radiating specific radiation to the bolus, and obtaining a radiation distribution that passes through the bolus using a film, an electronic portal imaging apparatus, or a radiation distribution measurement apparatus.

Thereafter, the obtained radiation distribution is overlapped with the radiation intensity modulation information, obtained by the radiotherapy treatment planning unit 100, based on the indication of the center of the radiation beam, and a comparison between the intensities of the pixels of the bolus is performed.

The comparison between the intensities of the pixels complies with the same method as the aforementioned statistical error evaluation and gamma analysis method.

In the actual radiotherapy treatment step using the bolus as illustrated in FIG. 5, the accuracy verification unit 400 displays the bolus included in the file of the planned bolus 320 in a 3D way so that a possibility that an error may occur due to the use of an erroneous bolus is reduced by checking whether or not the bolus is the bolus of a corresponding patient, and displays the patient ID and information related to the treatment unit 370 so that an error in the selection of a patient and an error in the selection of the treatment unit 370 are verified (S170).

As described above, the method and apparatus for manufacturing a radiation intensity bolus according to the present disclosure computes a 3D radiation dose distribution, plans the manufacturing a bolus, obtains information about the 3D structure of a bolus to be manufactured using radiation intensity modulation information, verifies the type, location, and size of the bolus to be manufactured, manufactures the bolus through a 3D printer, and evaluates manufacturing accuracy by performing a comparison with information about the planned bolus 320. Accordingly, an error due to the malfunction of a radiation collimator when an intensity modulated radiotherapy using a radiation collimator is performed can be prevented, an error in the calculation of a scattered dose generated in collimator gaps or leaves can be prevented, the treatment time can be significantly reduced compared to a conventional method using a collimator, and an intensity modulated beam can be accurately radiated when a moving internal organ is treated.

Furthermore, compared to a bolus manufacturing method using conventional cutting, noise generated in a cutting process can be reduced, the generation of a contaminated coolant can be prevented, bolus manufacturing is performed in a small space, and precision processing is available which prevents micromachining errors due to the size of a cutting drill. When a radiation intensity bolus is manufactured by 3D printing, metal effective in radiation shielding can be used as well as tissue-equivalent materials.

The system, method, components and units described in conjunction with figures may be implemented in the form of a computer-readable storage medium including computer-executable instructions, such as one or more computer-executable applications or modules.

The computer-readable storage medium may be any available medium that can be accessed by a computer, and includes volatile and nonvolatile media and removable and non-removable media.

Additionally, the computer-readable storage medium may include both a computer storage medium and a communication medium. The computer-readable storage medium may include volatile and nonvolatile media and removable and non-removable media that are implemented using any method or technology for storing information, such as computer-readable instructions, a data structure, a module or other types of data.

The term "module" or "unit" may refer to hardware capable of performing a function and operation based on the name of each component described herein, computer program code capable of performing a specific function and operation, or an electronic storage medium (or processor) on which computer program code capable of performing a specific function and operation has been installed.

While the embodiments of the present disclosure have been described above, those skilled in the art will understand that the present disclosure may be modified and changed in various ways within the spirit and scope of the present disclosure written in the following claims.

The invention claimed is:

1. A method of manufacturing a radiation intensity bolus, comprising steps of:
   (a) calculating, by a radiotherapy treatment planning unit, a received 3D radiation dose distribution, planning a bolus to be manufactured, and outputting radiation intensity modulation information;
   (b) receiving, by a bolus design unit, the radiation intensity modulation information, generating a conversion file for manufacturing bolus, and outputting information about a 3D structure of the bolus to be manufactured;
   (c) receiving, by a bolus manufacturing unit, the conversion file for manufacturing bolus, verifying a type, location, and size of the bolus to be manufactured, sending the verified data to a 3D printer, and manufacturing the bolus; and
   (d) obtaining, by an accuracy verification unit, information about a 3D structure of the manufactured bolus and evaluating manufacturing accuracy by comparing the information about the 3D structure of the manufactured bolus with the information about the planned bolus,
   wherein the size of the bolus to be manufactured is determined by calculating the 3D structure of the bolus to be manufactured in accordance with a distance inverse square law based on a location where the bolus to be manufactured is attached to a treatment unit, a radiation source, and a distance from a patient.

2. The method of claim 1, wherein the step (b) comprises steps of:
   calculating, by the bolus design unit, information about a thickness of each pixel of the bolus to be manufactured that is proportional to an amount of radiation intensity modulation;
   generating, by the bolus design unit, initial data by which the size of the bolus to be manufactured is calculated;
   generating, by the bolus design unit, an initial bolus of the bolus to be manufactured based on the initial data; and
   calculating, by the bolus design unit, information about the 3D structure and information about 3D coordinates of the bolus to be manufactured based on the initial bolus.

3. The method of claim 1, wherein the step (b) comprises:
   generating a periphery support that surrounds a periphery of the bolus to be manufactured and supports the bolus to be manufactured while the bolus is manufactured; and
   generating an attachment unit that attaches and fixes the manufactured bolus to a treatment unit.

4. The method of claim 3, wherein the step (c) comprises:
   reading, by the bolus manufacturing unit, the conversion file for manufacturing bolus, verifying the type, location, and size of the bolus to be manufactured, and verifying a type of the attachment unit; and sending, by the bolus manufacturing unit, the verified data to the 3D printer and manufacturing the bolus comprising the periphery support.

5. The method of claim 3, wherein the step (c) comprises including the attachment unit in the computed structure of the bolus so that the attachment unit and the bolus are manufactured simultaneously.

6. The method of claim 1, wherein:
the information about the 3D coordinates is 3D location coordinates where the bolus to be manufactured is placed based on an indication of a center of a radiation beam, and
an origin of the 3D location coordinates and axes of the 3D location coordinates are indicated on a surface of the bolus to be manufactured.

7. The method of claim 1, wherein the step (d) comprises displaying, by the accuracy verification unit, the bolus stored in the conversion file for manufacturing bolus during radiotherapy treatment so that an error in selecting a patient or a treatment unit is verified.

8. The method of claim 1, wherein the step (d) comprises steps of:
obtaining a periphery structure of the manufactured bolus and reconfiguring the manufactured bolus in a format to be compared with the planned bolus;
overlapping a 3D structure of the reconfigured bolus with a 3D structure of the planned bolus based on an indication of a center of a radiation beam and calculating a difference in a thickness in each pixel of the bolus; and
evaluating the manufacturing accuracy by diagramming the difference in the thickness in numbers and graphics.

9. The method of claim 8, wherein the periphery structure is obtained using any one of a 3D laser scanner, a video camera, and a touch sensor.

10. The method of claim 1, wherein the step (d) comprises steps of:
mounting the manufactured bolus on a treatment unit, irradiating the manufactured bolus, and obtaining a radiation distribution that has passed through the manufactured bolus;
measuring the obtained radiation distribution, overlapping the measured radiation distribution with the radiation intensity modulation information based on an indication of a center of a radiation beam, and performing a comparison between differences of radiation intensities of pixels of the bolus; and
diagramming the difference in the intensity in numbers and graphics and evaluating the manufacturing accuracy.

11. The method of claim 10, wherein the radiation distribution is obtained using any one of a film, an electronic portal imaging apparatus, and a radiation distribution measurement apparatus.

12. The method of claim 1, wherein the 3D radiation dose distribution is calculated using a radiotherapy treatment planning apparatus or manually.

13. The method of claim 1, wherein the size of the bolus to be manufactured is determined again after calculating an attenuation of radiation according to materials of the bolus to be manufactured using an attenuation coefficient or a stopping power ratio depending on the type of radiation.

14. The method of claim 1, wherein the conversion file for manufacturing bolus stores at least one of the type of material used to calculate the size of the bolus to be manufactured, a 3D structure, location coordinates, information identifying a corresponding patient, information about a treatment unit, and a radiation port.

15. An apparatus for manufacturing a radiation intensity bolus, comprising:
a radiotherapy treatment planning unit that calculates a received 3D radiation dose distribution, plans a bolus to be manufactured, and outputs radiation intensity modulation information;
a bolus design unit that receives the radiation intensity modulation information, generates a conversion file for manufacturing bolus, and outputs information about a 3D structure of the bolus to be manufactured;
a bolus manufacturing unit that receives the conversion file for manufacturing bolus, verifies a type, location, and size of the bolus to be manufactured, sends the verified data to a 3D printer, and manufactures the bolus; and
an accuracy verification unit that obtains information about a 3D structure of the manufactured bolus and evaluates manufacturing accuracy by comparing the information about the 3D structure of the manufactured bolus with the information about the planned bolus,
wherein the size of the bolus to be manufactured is determined by calculating the 3D structure of the bolus to be manufactured in accordance with a distance inverses square law based on a location where the bolus to be manufactured is attached to a treatment unit, a radiation source, and a distance from a patient.

16. The apparatus of claim 15, wherein the bolus design unit:
calculates information about a thickness of each pixel of the bolus to be manufactured that is proportional to an amount of radiation intensity modulation,
generates initial data by which the size of the bolus to be manufactured is calculated,
generates an initial bolus of the bolus to be manufactured based on the initial data, and
calculates information about the 3D structure and information about 3D coordinates of the bolus to be manufactured based on the initial bolus.

17. The apparatus of claim 16, wherein the bolus design unit:
generates a periphery support that surrounds a periphery of the bolus to be manufactured and supports the bolus to be manufactured while the bolus is manufactured, and
generates an attachment unit that attaches and fixes the manufactured bolus to a treatment unit.

18. The apparatus of claim 17, wherein the bolus manufacturing unit:
reads the conversion file for manufacturing bolus, verifies the type, location, and size of the bolus to be manufactured, and verifies a type of the attachment unit; and
sends the verified data to the 3D printer and manufactures the bolus comprising the periphery support.

19. The apparatus of claim 17, wherein the bolus manufacturing unit includes the attachment unit in the computed structure of the bolus so that the attachment unit and the bolus are manufactured simultaneously.

20. The apparatus of claim 16, wherein the accuracy verification unit displays the bolus stored in the conversion file for manufacturing bolus during radiotherapy treatment so that an error in selecting a patient or a treatment unit is verified.

21. The apparatus of claim 16, wherein the accuracy verification unit:

obtains a periphery structure of the manufactured bolus and reconfigures the manufactured bolus in a format to be compared with the planned bolus, overlaps a 3D structure of the reconfigured bolus with a 3D structure of the planned bolus based on an indication of a center of a radiation beam and calculates a difference in a thickness in each pixel of the bolus, and evaluates the manufacturing accuracy by diagramming the difference in the thickness in numbers and graphics.

22. The apparatus of claim 16, wherein the accuracy verification unit:

mounts the manufactured bolus on a treatment unit and irradiates the manufactured bolus so that the radiation passes through the manufactured bolus, measures a distribution of the transmitted radiation, overlaps the measured radiation distribution with the radiation intensity modulation information based on an indication of a center of a radiation beam, and performs a comparison between differences of radiation intensities of pixels of the bolus, and diagrams the difference in the intensity in numbers and graphics and evaluates the manufacturing accuracy.

\* \* \* \* \*